US011337841B2

(12) United States Patent
Gordon et al.

(10) Patent No.: US 11,337,841 B2
(45) Date of Patent: May 24, 2022

(54) METHODS AND DEVICES FOR SUPPORTING A PATIENT'S LEG TO INCREASE COMFORT AND ASSIST IN RECOVERY

(71) Applicants: Alexander Capel Gordon, Prospect Heights, IL (US); David Joseph Siers, Palatine, IL (US); Lawrence L. Gualano, Prospect Heights, IL (US)

(72) Inventors: Alexander Capel Gordon, Prospect Heights, IL (US); David Joseph Siers, Palatine, IL (US); Lawrence L. Gualano, Prospect Heights, IL (US)

(73) Assignee: DLA Medical LLC, Prospect Heights, IL (US)

( * ) Notice: Subject to any disclaimer, the term of this patent is extended or adjusted under 35 U.S.C. 154(b) by 399 days.

(21) Appl. No.: 15/897,802

(22) Filed: Feb. 15, 2018

(65) Prior Publication Data

US 2019/0247214 A1    Aug. 15, 2019

(51) Int. Cl.
| | | |
|---|---|---|
| A61F 5/01 | (2006.01) | |
| A61F 2/38 | (2006.01) | |
| A61G 7/07 | (2006.01) | |
| A61G 7/075 | (2006.01) | |
| A61G 13/12 | (2006.01) | |

(52) U.S. Cl.
CPC .............. *A61F 5/0116* (2013.01); *A61F 2/38* (2013.01); *A61G 7/07* (2013.01); *A61G 7/0755* (2013.01);
(Continued)

(58) Field of Classification Search
CPC .... A61F 5/019; A61F 5/37; A61F 5/11; A61F 5/0113; A61F 5/0116; A61F 5/0585;
(Continued)

(56) References Cited

U.S. PATENT DOCUMENTS

| | | | | |
|---|---|---|---|---|
| 3,256,879 A | * | 6/1966 | Hipps | A61F 13/069 |
| | | | | 128/892 |
| 3,742,528 A | * | 7/1973 | Munch | A47C 27/20 |
| | | | | 5/723 |

(Continued)

OTHER PUBLICATIONS

A M Fredriks, S van Buuren, W J M van Heel, R H M Dijkman-Neerincx, S P Verloove-Vanhorick, J M Wit, "Nationwide age references for sitting height, leg length, and sitting height/height ratio, and their diagnostic value for disproportionate growth disorders", Apr. 29, 2005, Arch Dis Child 2005;90:807-812 (Year: 2005).*

(Continued)

*Primary Examiner* — Erin Deery
*Assistant Examiner* — Daniel A Miller
(74) *Attorney, Agent, or Firm* — Vitale, Vickrey, Niro, Solon & Gasey LLP (57) ABSTRACT

The present disclosure relates to a support system for patients recovering from medical procedures, including from total knee replacement surgery. The disclosed system may include a foot support unit which supports a patient's feet, where the foot support may have leg grooves separated by a divider and a tapered height. The foot support may be placed in a patient's bed. Additionally hip support wedges may be placed beneath a patient's hip, where the hip supports provide the benefit of counteracting a leg's natural tendency to rotate outwards. The disclosed foot support and hip wedges promote proper alignment and in that way provide comfort and assist in recovery.

10 Claims, 10 Drawing Sheets

(52) U.S. Cl.
CPC ..... *A61G 13/1245* (2013.01); *A61G 13/1285* (2013.01)

(58) Field of Classification Search
CPC ......... A61F 2/038; A47C 27/10; A47C 20/00; A47C 20/021; A47C 20/02; A47C 16/00; A47C 16/02; A61G 13/1245; A61G 13/1285; A61G 13/123; A61G 13/125; A61G 13/129; A61G 13/1295; A61G 13/128; A61G 13/0081; A61G 13/0063; A61G 7/001; A61G 7/0525; A61G 7/057; A61G 7/05715; A61G 7/05761; A61G 7/065; A61G 7/1025; A61G 7/1082; A61G 7/1088; A61G 7/109; A47G 9/10; A47G 9/1018
USPC ........................................................ 128/845
See application file for complete search history.

(56) References Cited

U.S. PATENT DOCUMENTS

| | | | | |
|---|---|---|---|---|
| 5,216,772 A | * | 6/1993 | Clute | A47D 13/08 5/630 |
| 5,289,828 A | * | 3/1994 | Toth | A47C 20/021 128/DIG. 20 |
| 9,381,107 B2 | * | 7/2016 | MacLeod | A61F 5/3769 |
| 9,775,440 B1 | * | 10/2017 | Chon | A47C 20/021 |
| 9,901,491 B2 | * | 2/2018 | Squitieri | A61F 13/51474 |
| 2003/0230310 A1 | * | 12/2003 | Day | A61F 5/01 128/845 |
| 2004/0070254 A1 | * | 4/2004 | Conlon | A47C 16/02 297/423.41 |
| 2006/0278237 A1 | * | 12/2006 | Hinders | A61G 13/12 128/845 |
| 2009/0308400 A1 | * | 12/2009 | Wilson | A61N 5/1049 128/845 |
| 2012/0247484 A1 | * | 10/2012 | Jewell | A61G 7/057 128/845 |
| 2013/0319426 A1 | * | 12/2013 | Castle | A61F 5/30 128/845 |
| 2014/0190488 A1 | * | 7/2014 | Robran | A61F 5/01 128/845 |
| 2018/0008499 A1 | * | 1/2018 | Lucey | A61G 7/0755 |

OTHER PUBLICATIONS

Photograph showing the commercial embodiment of the hip wedges and foot support shown in Figs. 5 and 6.
Brochure of commercial embodiment of present inventions.

* cited by examiner

METHODS AND DEVICES FOR SUPPORTING A PATIENT'S LEG TO INCREASE COMFORT AND ASSIST IN RECOVERY

FIELD OF THE INVENTION

The present disclosures relate to methods and devices for providing support for users, and in particular users who are patients recovering from total knee replacement or other medical procedures. The present disclosures may assist patients who must sleep on their back when recovering from procedures, or for any other reason. In a preferred embodiment, the inventions disclosed herein include a foot support which holds one or both of a patient's feet; and also one or two hip support wedges which may be positioned underneath a patient's hip(s) to prevent the patient's legs and feet from rotating outwards, which would be undesirable for the patient's comfort and recovery. In this way, the systems and methods of the present disclosure may provide physical support to a patient's legs and thereby assist in recovering from medical treatment.

BACKGROUND OF THE INVENTION

There is an increasing need for new methods and devices that provide support to patients recovering from medical procedures, including (but not limited to) total knee replacements (sometimes referred to as "TKRs"). For example, as total knee replacements become more common, there is a need for methods and devices that can support patients' lower extremities comfortably during recovery while they rest on their backs. Patients undergoing total knee replacement have reported extended periods of sleep disturbance. See e.g. Chen, A F, et al, *Prospective Evaluation of Sleep Disturbances After Total Knee Arthroplasty*, J. Arthroplasty 2016 January; 31(1):330-2. doi: 10.1016/j.arth.2015.07.044. Epub 2015 Aug. 30.

Herein, applicants disclose devices and methods for using said devices which provide advantages over prior art and satisfy long-felt but unsolved needs relating to patient recovery. The success of applicants' inventions has been demonstrated during applicants' own confidential testing. Subsequent to the present filing, applicants' inventions will be tested pursuant to a study protocol under review from Advocate Health Care Institutional Review Board, under project title [1182156-1] "Does an Orthopedic Sleep Device Improve Quality of Sleep After Total Knee Arthroplasty?" The Principal Investigator will be Alexander C Gordon, MD, one of the named inventors, who is an orthopedic surgeon. It is expected that the study results will demonstrate the invention's success and further bolster the novelty and non-obviousness of the present inventions.

Embodiments of the invention contribute to improve patients' sleep quality during surgical recovery. Moreover, narcotic pain medication is frequently used after knee surgery to combat poor sleep quality and pain. By increasing comfort, using embodiments of the invention may decrease the need for narcotic medications after surgery.

Rehabilitation after TKR is expensive, often painful, and time consuming, due to the change in patients' lower extremity alignment. The inventions disclosed herein allow a person to comfortably sleep on their back various embodiments of the present disclosure lock them into the back-sleeping position while aiding in regaining the proper leg extension by passively stretching the knee joint during rest. Disclosed embodiments also aid the greater percentage of TKR patients that have pre-existing deformities to assist in the passive development of proper hip alignment. Although the present disclosure may refer to the inventions used in the context of TKR patients, it should be understood that the inventions may be used with any person that has a need to sleep on their back due to other medical procedures. Examples of such additional medical procedures include cardiac patients, lower and upper extremity injuries, spine surgery patients, and eye surgery patients.

The embodiments disclosed herein provide many distinctions and benefits over prior art devices. For example, U.S. Pat. Nos. 6,634,045 and 6,935,697 disclose various cushions which can elevate and support a patient's leg(s). However, the prior art devices have numerous disadvantages. One such disadvantage is that the prior art devices do not provide support to counteract the natural tendency of a leg to rotate outward. Such external rotation is undesirable because it causes a patients' legs, and specifically the knee, to take a position which is detrimental to healing and comfort after a total knee replacement, which may lead to increased use of analgesic medication.

Additional disadvantages of the prior art devices include the fact that they are not adjustable and cannot accommodate patients with different sized legs. When used in a clinical setting, it may be necessary to accommodate patients of different sizes. Requiring a facility to keep a stock of devices in different sizes is disadvantageous.

Yet a further disadvantage of the prior art is that prior art devices do not provide for positioning a patient's heel and therefore do not cause the patient's lower leg (e.g. from the knee to the ankle) to lay perfectly flat (with respect to the ground). This short coming is a further disadvantage of using the prior art devices in recovering or rehabilitating a patient.

Thus, there exists a need for a new and improved device which can comfortably support a patient's legs in a "flat," or horizontal, position, while accommodating patients having different sized legs. Moreover, it would be advantageous to provide a device which can counteract the natural tendency of legs to rotate outward, because such outward motion may be detrimental to the recovery from total knee replacement or other medical procedures.

BRIEF SUMMARY OF THE DISCLOSURE

The present inventions build on, and improve, on the current state of the art relating to devices which help patients recover from medical procedures generally, including without limitation patients of total knee replacements (referred to as "TKR" herein).

For example, certain embodiments of the present disclosure include a system for aiding a patient in recovering from a medical procedure, the system including a foot support having a height, length, and depth, and a first and second leg groove extending perpendicularly across the foot support and separated by a divider having a divider and a first and second hip wedge, the first and second hip wedge each having a rectangular prism shape. In some embodiments, the first and second leg grooves are tapered, and may be tapered from a narrower portion having a narrower width of 3 inches to a wider portion having a wider width of 4.875. The first and second leg grooves may each have one heel cup positioned in the narrower portion, and in some embodiments, the heel cups may be 3 inches in diameter.

In some embodiments of the disclosure, foot support accommodates a 12-inch hip width. That is to say, the combined width of the first and second leg grooves, combined with the width of the divider, may be 12 inches. The foot support's height may be tapered from a first height of 6 inches to a second height of 8 inches. Moreover, in some embodiments, the foot support's width is approximately 22 inches, and the foot support's depth is approximately 13 inches. Further yet, the first and second hip wedges may each have a height of approximately 5.25 inches, and a width of approximately 10.29 inches.

Embodiments of the disclosure extend to a method for treating a total knee replacement patient, comprising the steps of providing a supine patient with a foot support having a height, length, and depth, and a first and second leg groove extending perpendicularly across the foot support from the foot support's proximal end to the foot support's distal end, the first and second leg groove being separated by a divider; placing the foot support on a planar surface, wherein the planar surface is a bed; placing the patient's first leg into the first leg groove and the first heel into the first heel cup, and the second leg into the second leg groove and the second heel into the second heel cup; providing a first and second hip wedge, each having a rectangular prism shape, and placing the first and second hip wedge on the planar surface; and positioning the first hip wedge below the patient's left hip and positioning the second hip wedge below the patient's right hip.

DETAILED DESCRIPTION OF THE PREFERRED EMBODIMENTS

Set forth below is a description of what are currently believed to be the preferred embodiments or best representative examples of the inventions disclosed and claimed herein. Present and future representations or modifications to the embodiments and preferred embodiments are also contemplated. It should be understood that the inventions are not limited in its application to the details of construction and the arrangement of components set forth in the following description or illustrated in the drawings. The invention is capable of other embodiments and of being practiced or carried out in various ways. The following discussion is presented to enable a person of ordinary skill in the art to make and use embodiments of the invention.

Moreover, to the extent that the present disclosure provides dimensions, such dimensions are provided in inches, and a person of skill in the art would understand that such dimensions are approximate, and that the manufacturing process should allow for manufacturing tolerances which are customary in the art.

Certain embodiments of the invention address issues relating to the recovery and rehabilitation of patients following medical procedures. In one example, embodiments disclosed herein address sleeping issues reported by the majority of TKR patients, but it should be understood that the inventions are not limited to use in TKR patients. It is intended that embodiments of the inventions could be used by patients in the clinical setting (for example, in hospital beds) but also in patients' homes.

Specifically, some embodiments of the invention address a common issue with the recovery from TKR, which is the positioning of a patient's legs while sleeping. Even when sleeping on their backs, patients often suffer from prolonged recovery and increased pain because patients' extremity have a tendency to turn outward due to their pre-existing disease state, and such outward rotation causes stress and torque on the knee, thereby making rehabilitation more difficult and sleeping more uncomfortable. This is particularly true in TKR patients who often have had a bow-legged to knock-knee deformity corrected and part of the surgical procedure. Embodiments of the invention counteract the malrotation of the leg and, in that way, promote proper knee and hip alignment, which aids in recovery. Embodiments of the inventions also promote regaining proper leg extension by passively stretching the knee joint while sleeping.

Figure 1A:
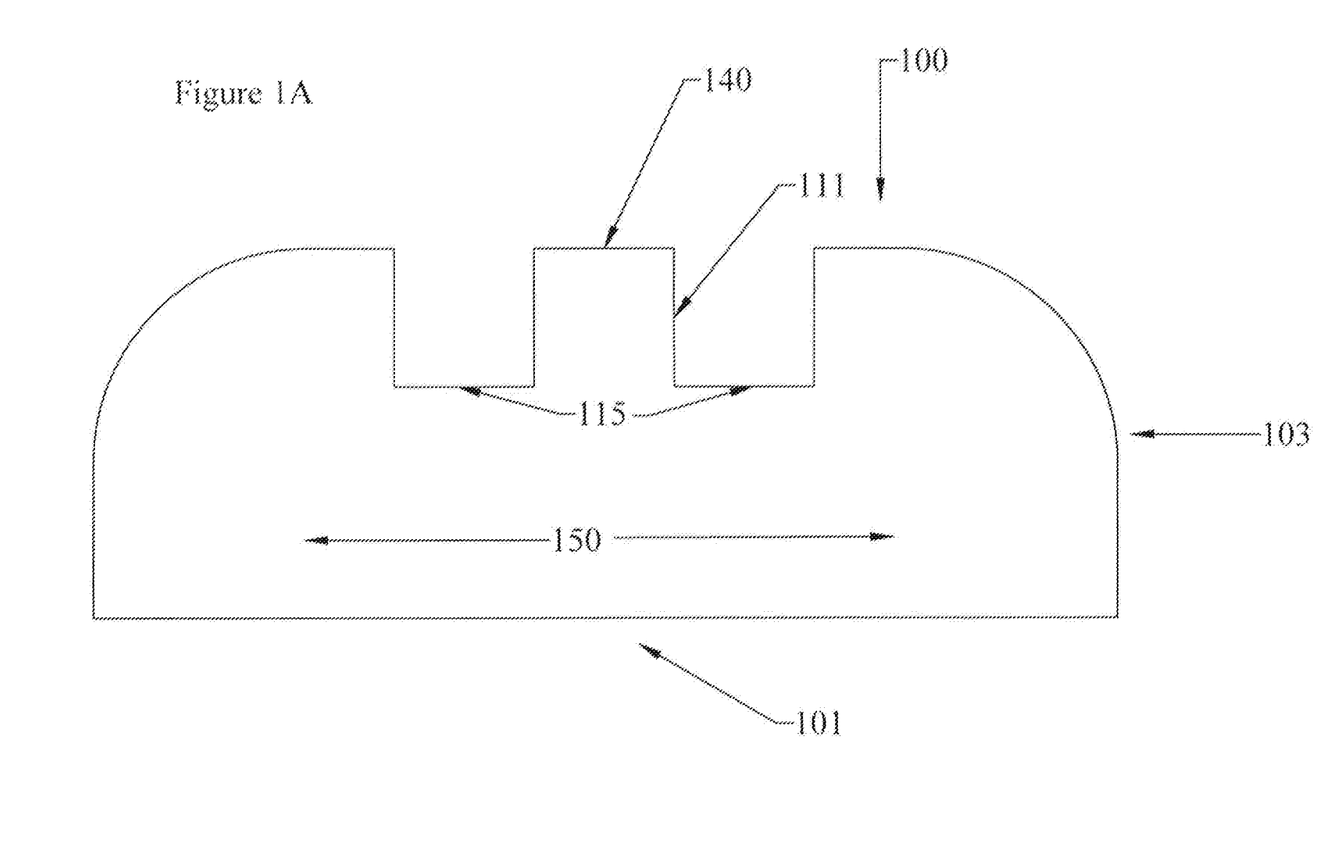
FIG. 1A is a view, from a front angle, of an embodiment of the foot support disclosed herein.

Turning first to FIG. 1A, a foot support 100 is shown (from a side-view) which may be used to support one or both of a patient's foot/feet. In preferred embodiments, the foot support 100 may be formed of foam or a similar material. In embodiments where foot support 100 is formed of foam, it may be desirable to use colored foam because white foam has a tenancy to discolor, which may become unattractive to patients and thereby cause patients to forego use of the inventions. One consideration is providing comfort to a patient while supporting the patient's foot, and foam is particularly well suited for this purpose (in part because of its breathability). However, it should be understood that this disclosure contemplates that foot support 100 could be formed from any possible material, including without limitation rubber or plastic.

Figure 1B:
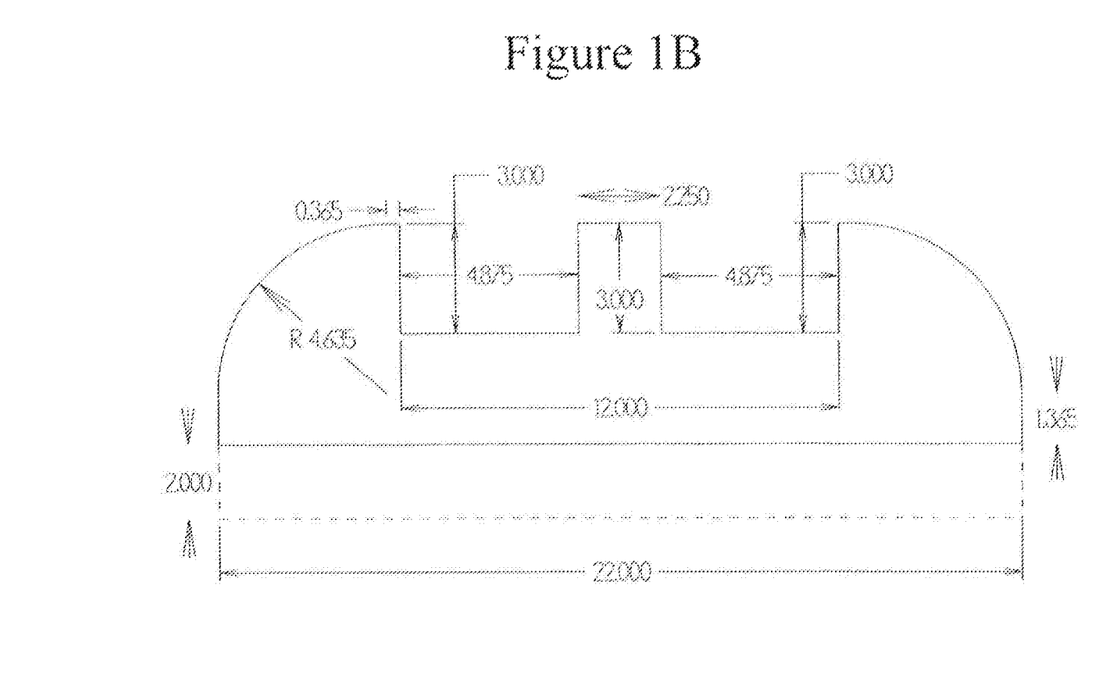
FIG. 1B is a view, from a front angle, of an embodiment of the foot support disclosed herein with exemplary dimensions disclosed.

In embodiments of the invention, foot support 100 may be generally rectangular with a depth 102 of 13 inches (See FIGS. 2A and 3B) and a length 101 of 22 inches. FIG. 1B provides exemplary dimensions, in inches, which may be used to manufacture foot support 100, but does not limit the invention to only the dimensions shown. Additionally, some embodiments of the invention may have a generally uniform height 103, for example approximately 8 inches. Other embodiments of the inventions may have a tapered height of 6 inches on one end and 8 inches on the other, as seen for example in FIGS. 2A and 2B, wherein foot support 100 is shown to have a height 103 on one edge (which is the proximal edge) and a second height 104 on a second edge (which is the distal edge). In FIG. 2B, these heights are shown as 6 and 8 inches, respectively, wherein the contemplated orientation has the lesser height 103 oriented closer (proximal) to the patient.

Figure 2A:
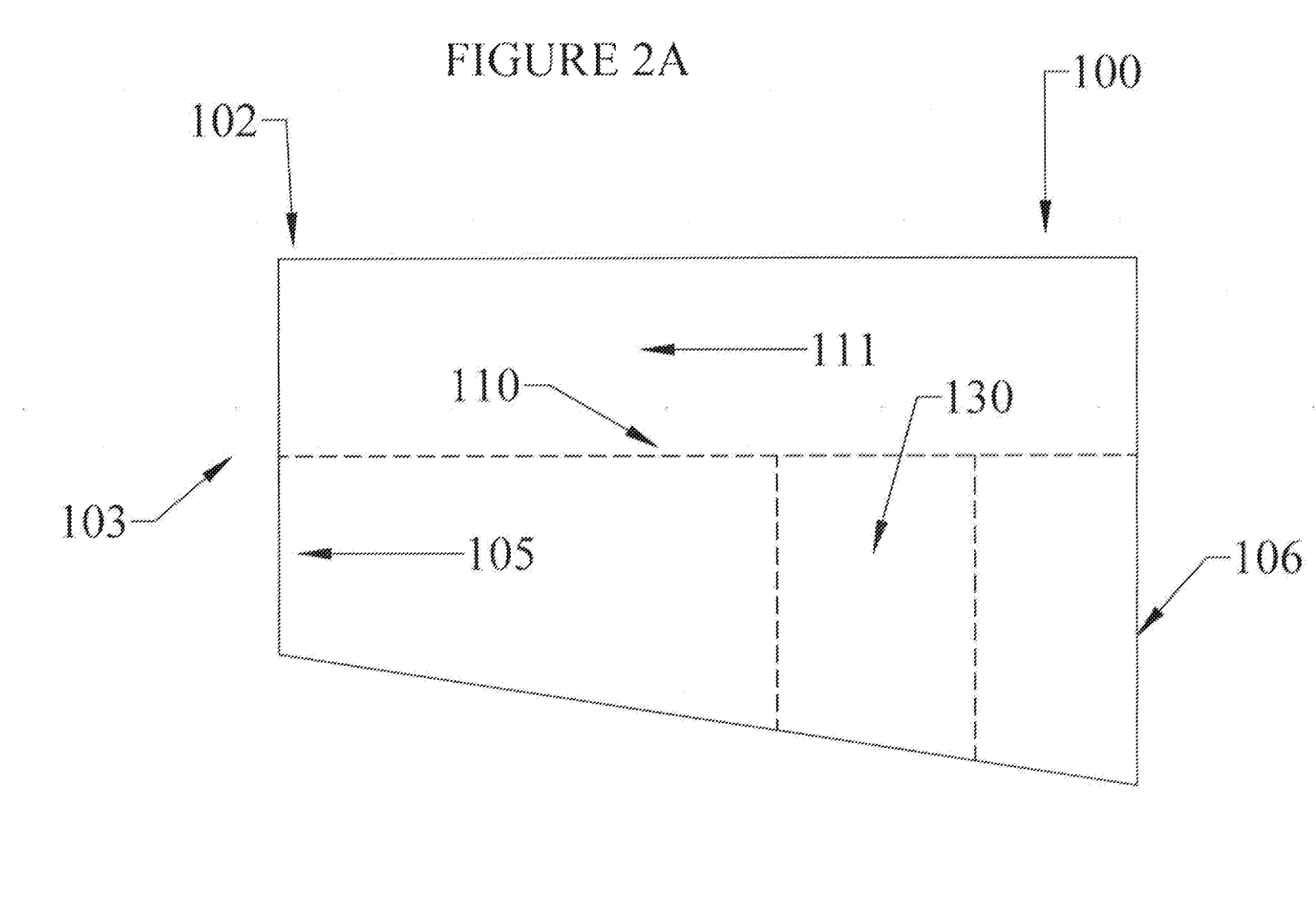
FIG. 2A is a view, from a side angle, of an embodiment of the foot support disclosed herein.
Figure 2B:
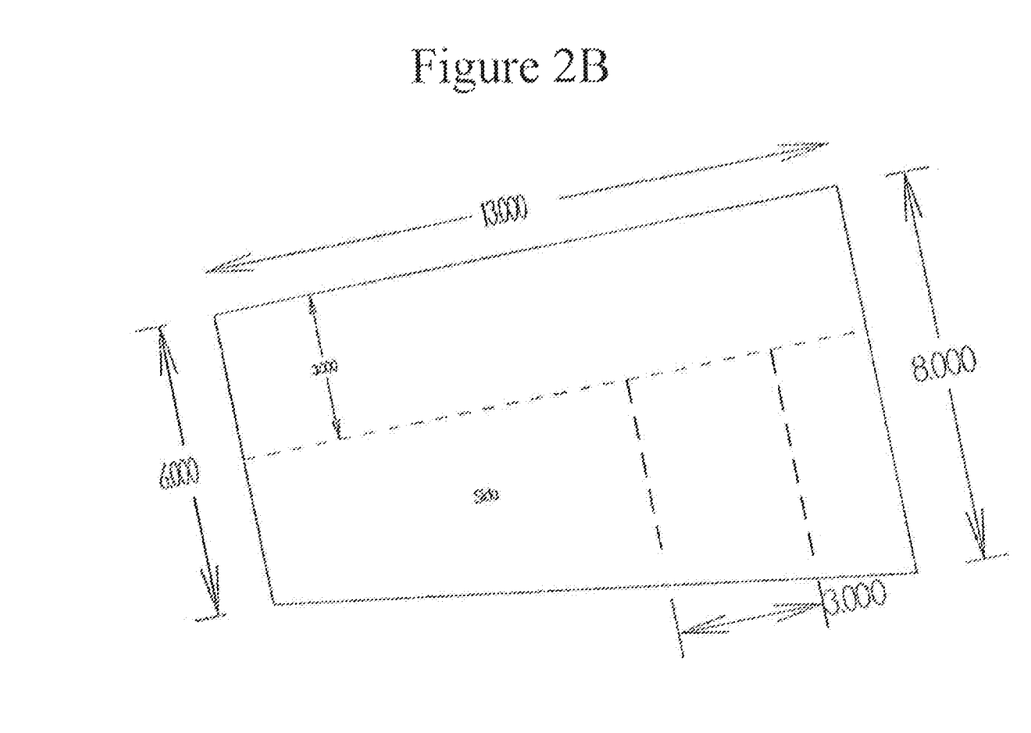
FIG. 2B is a view, from a side angle, of an embodiment of the foot support disclosed herein, with exemplary dimensions disclosed.

Moreover, FIGS. 2A and 2B show that the leg grooves 110 may slope from a height 105 of 3 inches to a height 106 of 5 inches. In such an embodiment, the divider 140 may have a height 111 of three inches, and the height of leg grooves 110 may slope from 105 (e.g. 3 inches) to 106 (e.g. 5 inches). It thus follows that, in some examples, foot support's height ranges from 103 (6 inches) to 104 (8 inches). Embodiments having a tapered height have the benefit of sloping towards a patient (when laid on a flat surface such as a bed), which is discussed further herein. These exemplary dimensions provide the benefit of comfortably fitting within a patient's bed and are similar in dimension to a standard bed pillow, providing the benefit of easy storage when not in use. However, it should be understood that, in light of this disclosure, other dimensions are possible.

Figure 3A:
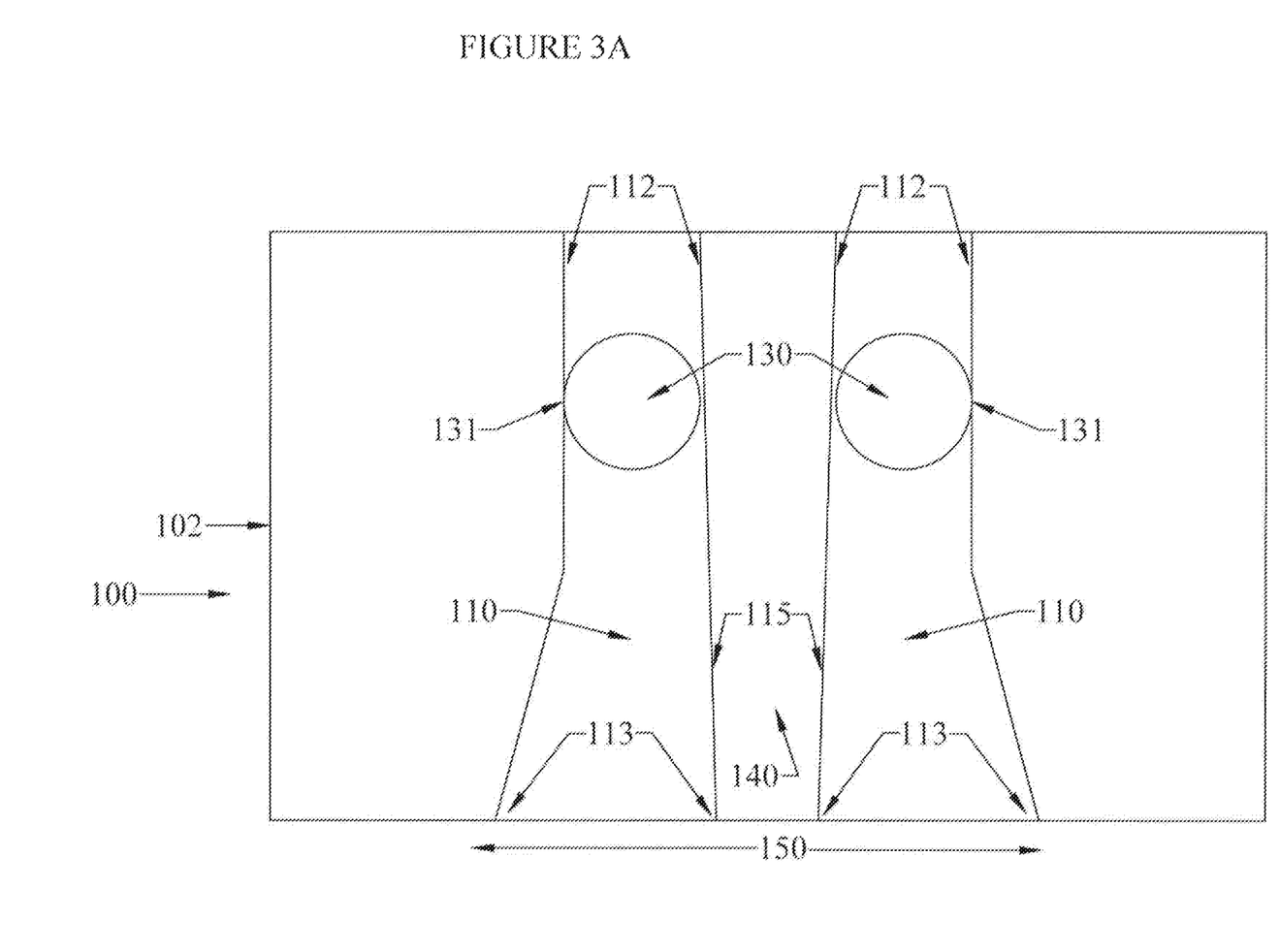
FIG. 3A is a view, from the top down, of an embodiment of the foot support disclosed herein.

Turning now to FIG. 3A, foot support 100 may include one or two leg grooves 110 which are formed in foot support 100. Leg grooves 110 are separated by divider 140. Although embodiments for use with two feet are shown, it should be understood that the present inventions also include embodiments having support for one leg. Both embodiments are contemplated in this disclosure.

The leg groove(s) 110 may run generally perpendicular across foot support 100, and be separated by a divider 140. In embodiments of the inventions, divider 140 may have a depth 111 (See FIG. 1) of approximately 3 inches. The height of leg grooves 110 may vary and slope downward towards a patient as seen in FIG. 2A, where the height of leg grooves 110 is seen to vary, i.e. slope, from a first height 105 to a second height 106. In such embodiments, when laid on a flat surface such as a bed, the varying height results in a downward slope of leg grooves 110. Preferably, the slope is orientated to slope downwards to a patient. For that reason, this disclosure may refer to height 105 as the proximal end (e.g. the end closer to a patient) and the height 106 as the distal end (e.g. the end further away from a patient).

In some embodiments, the first height of leg grooves 110 may be 3 inches at the proximal end (e.g., height 105), and the second may be 5 inches at the distal end (e.g. height 106). Such a sloped height creates leg grooves 110 which slope downward towards a patient. Applicant's confidential and preliminary testing indicates that said downward slope towards a patient provides increase comfort and benefits in recovery.

Figure 3B:
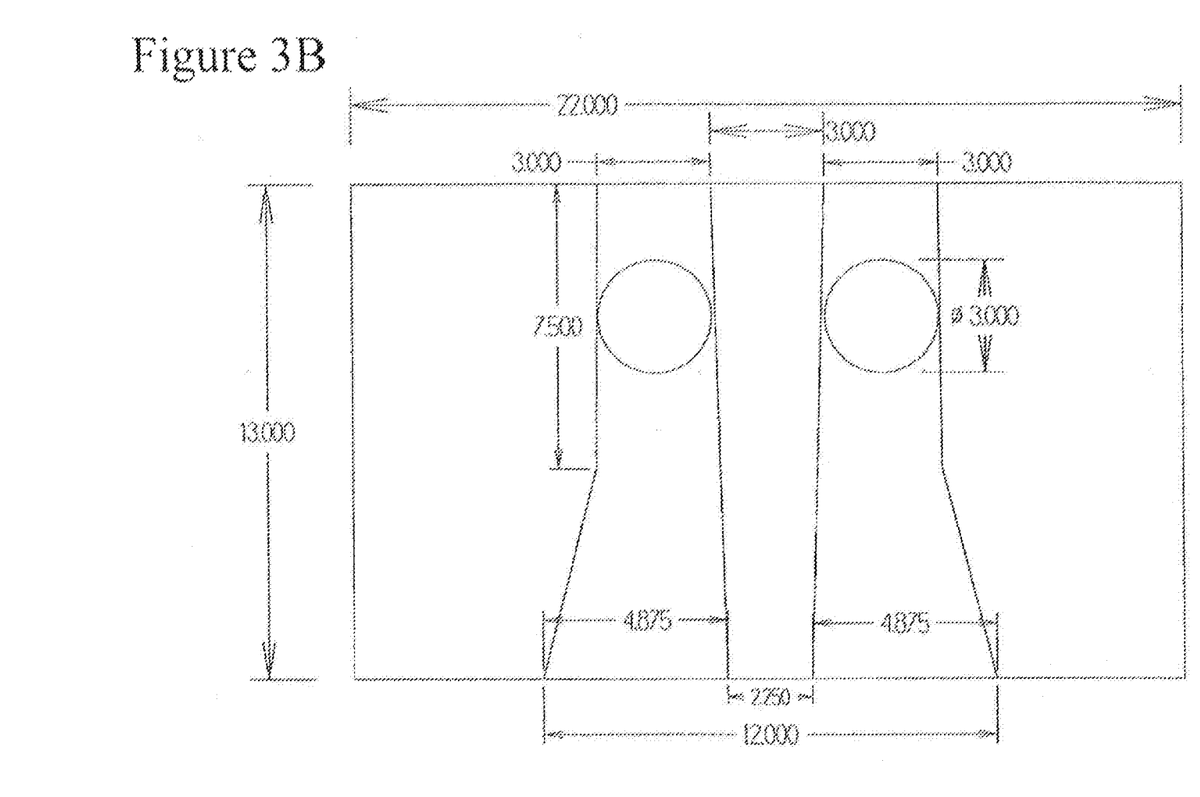
FIG. 3B is a view, from the top down, of an embodiment of the foot support disclosed herein, with exemplary dimensions disclosed.

As indicated in FIGS. 3A and 3B, each leg groove may have a width 112, which may be approximately 3.3 inches. In some embodiments of the invention, leg grooves 110 may be tapered. Thus, leg grooves 110 may have a narrower portion having a narrower width of 3.3 inches and a wider portion having a wider width 113 of 4.875 inches. The narrower portion, in which heel cups 130 are positioned, is oriented relatively distal to the patient while the wider portion is proximal. The wider width 113 allows patients of different sizes to still fit comfortably within leg grooves 110, while also maintaining a tight fit around the patients' lower leg (e.g. the wider width may accommodate a patient's calf). These dimensions are optimized to allow a neutral position for the patient's leg, while maintaining support for comfort and optimization of limb alignment.

Moreover, as further seen in FIG. 3A, heel cups 130 may be provided. A patient using foot support 100 may rest their heels in heel cup(s) 130 which allows the patient's lower leg to lay flush with leg grooves 110 and relieves pressure from the heel. In the absence of heel cups 130, the weight of the patients' heel may cause ulceration of the skin, which is a major complication after TKR and other procedures. In embodiments of the inventions, heel cup(s) 130 may have a diameter 131 of 3 inches, although a person of skill in the art would understand that their size may be varied depending, for example, on the size of a patient.

As also seen in FIG. 3A, divider 140 may have a divider width 115 which is the width separating a patient's legs. The divider width 115 combined with the width of two leg grooves 110 is the width corresponding to a patient's hip width 150. In preferred embodiments, the divider width 150 may be 2.250 inches, and the leg grooves 110 may each have a width of 4.875 inches, adding up to a combined patient's hip width 150 of 12 inches. Such exemplary dimensions are illustrated in FIG. 3B. By configuring a patient's hip width 150 to be 12 inches, embodiments of the invention will fit the majority of patients because the 12-inch width corresponds to the most common hip width. A person of skill in the art would understand that the dimensions described are approximate, and also that other dimensions can also be selected.

Furthermore, embodiments of the invention may include means for varying width depending on a patient. In such embodiments, foot support 100 may be comprised of two single, modular components which are attached to one another by a fastener, such Velcro, or any other fastener known in the art. Such embodiments may receive a spacer (not shown) which can be configured between the two modular components for increasing the space between leg grooves, and thereby accommodating patients with larger hip widths. Conversely, the spacers may be removed to narrow the width and accommodate smaller patients. In this way, foot support 100 may be adjustable to expand to fit patients of various sizes.

Figure 4A:
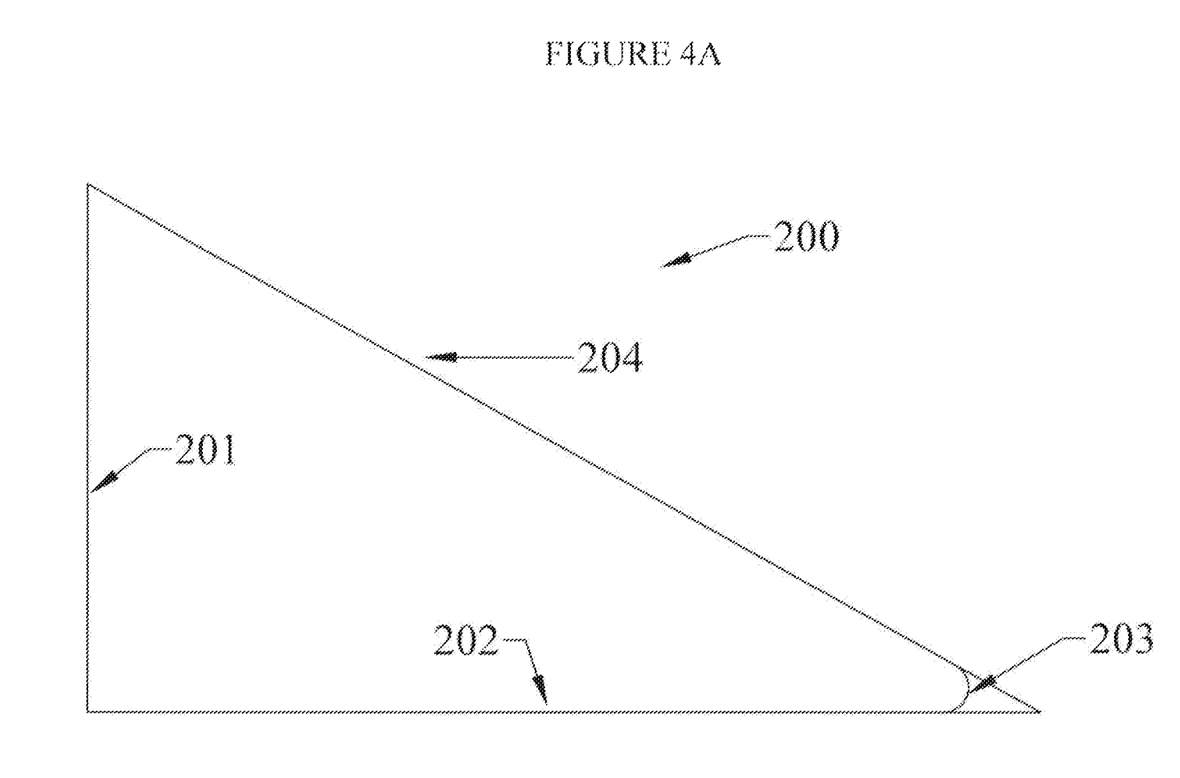
FIG. 4A is a view, from the side, of an embodiment of the hip wedge disclosed herein.
Figure 4B:
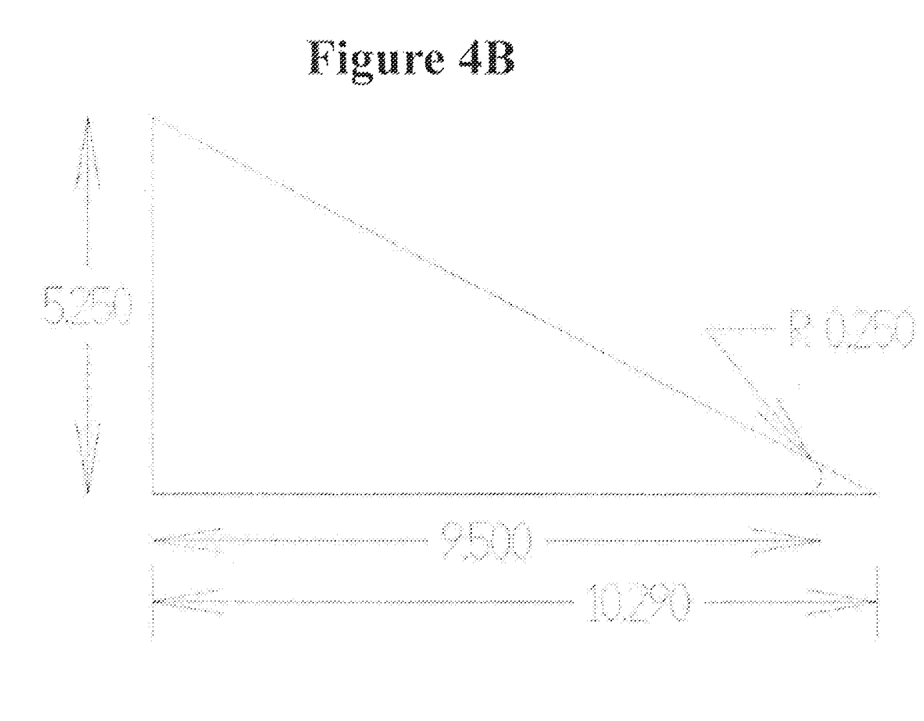
FIG. 4B is a view, from the side, of an embodiment of the hip wedge disclosed herein, with exemplary dimensions disclosed.

Turning now to FIGS. 4A and 4B, an embodiment of hip wedge 200 is shown from a side-view. In the embodiment shown in FIG. 4B, the hip wedge is approximately 5.25 inches in height 201 and 10.29 inches in width 202. The depth (not shown) may be 12-15 inches. It can be seen that hip wedge 200's surface takes a generally triangular shape, thereby forming a wedge. Together with the depth, the generally triangular surface forms a triangular prism. Hip wedge 200 is intended to be positioned under a patient's hip, and is thus oriented on the proximal end relative to foot support 100. As seen in FIG. 4, hip wedge 200 may have a rounded corner 203 of approximately 0.5-0.75 inches, which is optionally provided to increase a patient's comfort. In preferred embodiments, hip wedge 200 is formed out of foam, although other materials, including plastics and rubber, are also contemplated within this disclosure. A person of ordinary skill in the art would understand that the dimensions and materials of hip wedge 200 may vary, and still be within the scope of this disclosure.

Figure 5:
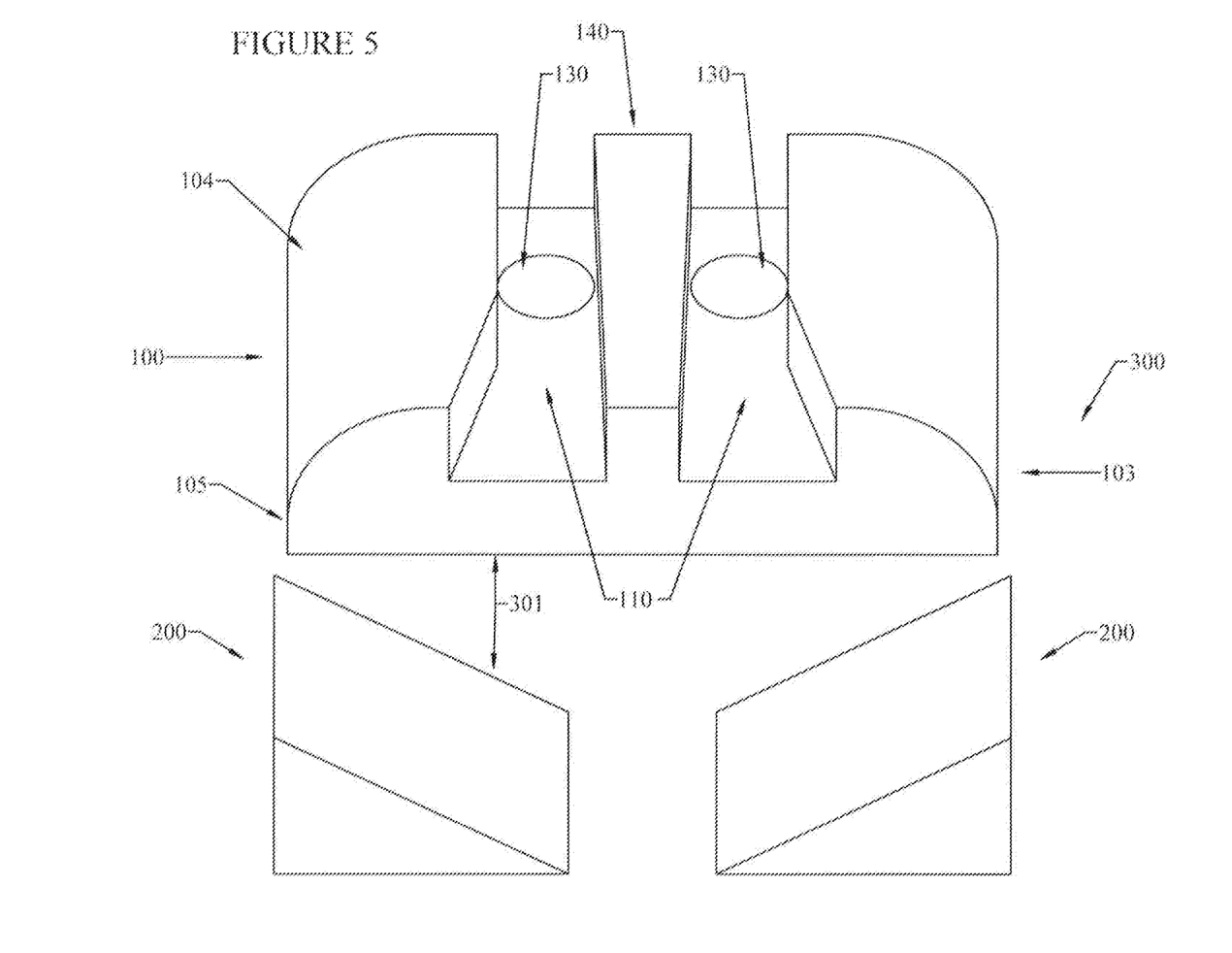
FIG. 5 shows an embodiment of the disclosed foot support, and two hip wedges positioned at the foot support's proximal edge.
Figure 6:
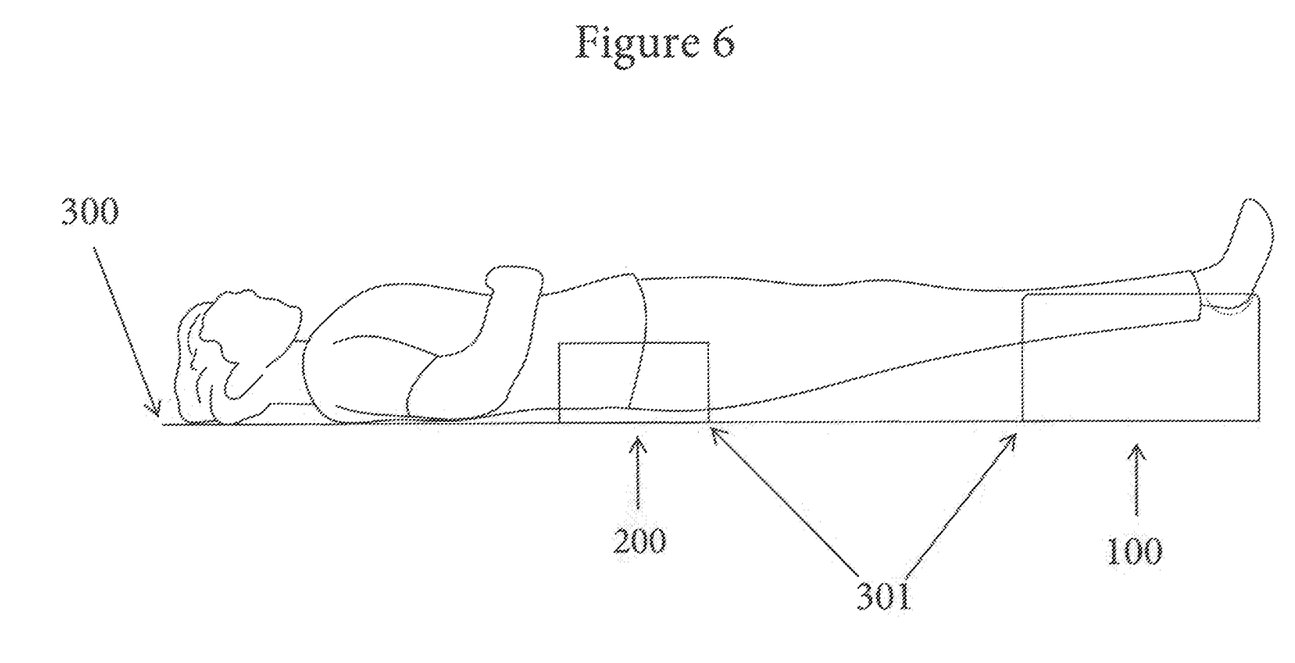
FIG. 6 shows a side view of a patient laying in a supine position on a surface, the patient's legs supported by the disclosed foot support, with a hip wedge positioned underneath the patient's hip.

Turning now to FIG. 5, an embodiment is disclosed wherein two hip wedges 200 are positioned at a proximal orientation to foot support 100, both on a planar surface 300 (such as a patient's bed). It can be seen that the hip wedges 200 are spatially positioned at the foot support's proximal edge and on the same surface 300. That is to say, from a patient's perspective, hip wedges 200 and foot support 100 may both be positioned on a bed surface, wherein hip wedges 200 are oriented at the foot support 100's proximal edge. A person of skill in the art would understand that, in this context, the spatial orientation of the hip wedges 200 at the foot support 100's proximal edge means that the hip wedges 200 are positioned "in front of" the foot support 100 at a spacing which accommodates a patient's hips. A patient may lay on their backs, supporting the hips on hip wedges 200 and positioning the legs in leg grooves 110, which are separated by divider 140. As discussed above, heel cups 130 may fit a patient's heels as the patient's legs are positioned in leg grooves 110. The spacing of hip wedges 200 relative to foot support 100 on surface 300, indicated in FIG. 5 by reference number 301, may be adjusted to fit a patient's size such that the patient's heels fit within heel cups 130 and hip wedges 200 fit below a patient's hips. It is contemplated that such spacing (e.g. 301) may range from 12 to 36 inches, depending on a patient's size and height, however a person of skill in the art would understand that such range is adjustable to accommodate a patient.

The present inventions extend to methods of treating patients using the devices disclosed herein. Patients recovering from TKR, but also from other medical procedures, as already explained above, will benefit from the use of foot support 100 to provide proper leg (and knee) extension and positioning. A patient laying on their back may place their legs in leg grooves 110 and their heels in heel cups 130, while using foot support 100, for example while laying in bed. Leg grooves 110 are configured to provide support to the patient's legs—for example, the outer edge of a leg groove 110 may provide support to patient's who are bow legged. Likewise, patients who are knock-kneed will be supported by the inner edges of leg grooves 110, e.g. by divider 140. In this way, foot support 100's leg grooves 110 provide support and assist a patient in maintaining a position which assists in recovery or rehabilitation.

For most patients, the length of leg grooves 110 will provide support up to the upper calf. A patient who is locked in to foot support 100 and hip wedge 200 may thus have an airspace, or gap, extending from below the patient's upper calf to the patient's thigh. This airspace, or gap, may be beneficial to some patients as it allows the leg(s) to be passively stretched, thus passively stretching a patient's joint(s) to gain extension. Gaining such extension may be desirable depending on the circumstances of the patient's procedure.

In other instances, patients may find added comfort from resting a pillow beneath their upper calf and/or knee and/or thigh. That is to say, it is contemplated that the disclosed foot support 100 may be positioned under a patient's heel and lower calf, while a standard pillow can be inserted below the upper calf and/or knee and/or thigh for added comfort. In this way, a pillow may provide support to the portions of a patient's legs in the gap between foot support 100 and hip wedge 200. Whether a patient prefers to include a pillow for support between the foot support 100 and hip wedge 200 may vary on a patient-by-patient basis.

Regardless of whether a pillow is used, it is contemplated that hip wedge 200 is placed under one or both of a patient's hips. In other words, as a patient is lying on their backs (also referred to as the supine position), a first and/or second hip wedge 200 is placed under each of the patient's hips, respectively. The patient's hips are supported by the respective hip wedge 200's top surface, indicated as surface 204 in FIG. 4A. The first and second hip wedge 200 may be placed into position by a medical professional, or by the patient themselves. For example, in a medical setting, a patient may assume the supine position, and then a professional may insert a first and second hip wedge underneath the patient's respective hips. It is also contemplated that patients may slide a first and second hip wedge 200 underneath the patient's own hips, or that a patient may position a first and second hip wedge on a bed prior to lying down.

To ensure that hip wedge(s) 200 stay in position, it is contemplated that the bottom surface, i.e. along width 202, may be formed out of a material which does not slide, such as rubber. A person of skill in the art would understand that it is not necessary for the entire bottom surface to be formed of, or coated in, rubber. It may be sufficient to provide rubber feet, for example by affixing a rubber foot to each corner of the bottom of hip wedge.

Hip wedge(s) 200 are an important aspect of the present preferred embodiments because, when used in conjunction with foot support 100, they provide the previously unknown benefit of reducing and/or preventing the tendency of a patient's leg(s) to rotate outwards. As described above, the outward rotation is detrimental to a patient's recovery, and may also lead to discomfort. In this way, use of the inventions disclosed herein provides improved comfort and improved recovery from medical procedures compared to prior art devices.

While aspects of the inventions have been described with reference to their preferred embodiments, it will be appreciated that numerous variations, modifications, and alternate embodiments are to be regarded as also being within the scope and spirit of the inventions.

Further, it should be understood that various changes and modifications to the preferred embodiments described herein would be apparent to those skilled in the art. Changes and modifications can be made without departing from the spirit and scope of the present invention and without diminishing its intended advantages.

What is claimed:

1. A method for aiding a patient in recovering from a medical procedure, comprising:
   positioning the patient in a supine position on a surface such that both shoulder blades of the patient contact the surface;
   positioning a foot support on the surface, the foot support having a length, a width, and depth, and a first and second leg groove extending perpendicularly across the foot support from a proximal end of the foot support to a distal end of the foot support, the first and second leg groove being separated by a divider, wherein the first and second leg groove each comprise a heel cup having a diameter of 3 inches, and the heel cups are configured to hold the patient's heels such that the patient's heels are prevented from rotating from a position where the patient's feet are perpendicular to the surface;
   positioning the patient's first and second legs in the first and second leg grooves, respectively, and positioning the patient's heels in the heel cup of the first and second leg groove so as to lay the patient's lower leg flush with the first and second leg grooves; and
   reducing a tendency of the patient's first and second legs to rotate outward by positioning a first hip wedge and second hip wedge underneath the patient's first and second hip, the first hip wedge having a first upper edge and a first lower edge and a width between the first upper edge and the first lower edge and the second hip wedge having a second upper edge and a second lower edge and a width between the second upper edge and the second lower edge, the first hip wedge is positioned underneath the patient such that the first upper edge of the first hip wedge is aligned with a waist of the patient and the first lower edge of the first hip wedge is aligned with a buttocks of the patient and the second hip wedge is positioned underneath the patient such that the second upper edge of the second hip wedge is aligned with the waist of the patient and the second lower edge of the second hip wedge is aligned with the buttocks of the patient, whereby the first hip wedge and second hip wedge prevent external rotation of the first hip and second hip respectively, while maintaining the patient in the supine position on the surface;

maintaining a spatial relationship defined between the proximal end of the foot support and first upper edge of the first hip wedge and the second upper edge of the second hip wedge, respectively, and the spatial relationship ranges between 12 to 36 inches to maintain the patient's knee in a position such that the knee gains passive extension due to gravity;

wherein the leg grooves have a height of 3 inches at the proximal end and 5 inches at the distal end; and wherein the first hip wedge and second hip wedge have a triangular prism shape, and the first hip wedge and second hip wedge are spatially oriented at the foot support's proximal end.

2. The method of claim 1, wherein the first and second leg grooves are each tapered from a narrower portion to a wider portion, and wherein the narrower portion is at the distal end of the foot support and the wider portion is at the proximal end of the foot support.

3. The method of claim 1, wherein the first and second leg grooves and the divider have a combined width of 12 inches.

4. The method of claim 1, wherein the foot support has a height that is tapered from a first height of 6 inches to a second height of 8 inches.

5. The method of claim 1, wherein the foot support has a height that is approximately 8 inches, the foot support's width is approximately 22 inches, and the foot support's depth is approximately 13 inches.

6. The method of claim 1, wherein the first and second hip wedges each have a height of approximately 5.25 inches, and a width of approximately 10.29 inches.

7. The method of claim 1, wherein the spatial relationship is 12 inches.

8. The method of claim 1, where in the spatial relationship is 36 inches.

9. The method of claim 1, wherein the width between the first upper edge and the first lower edge is approximately 10 inches and the width between the second upper edge and the second lower edge is approximately 10 inches.

10. The method of claim 1, wherein the width between the first upper edge and the first lower edge is 10 inches and the width between the second upper edge and the second lower edge is 10 inches.

* * * * *